US011090328B2

(12) United States Patent
Hwang et al.

(10) Patent No.: US 11,090,328 B2
(45) Date of Patent: *Aug. 17, 2021

(54) COMPOSITIONS AND METHODS FOR TREATING JOINTS

(71) Applicant: DePuy Mitek, LLC, Raynham, MA (US)

(72) Inventors: Julia Hwang, Wayland, MA (US); Dongling Su, Franklin, MA (US); Julius Lopez, Dorchester, MA (US)

(73) Assignee: Medos International Sarl, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/030,955

(22) Filed: Jul. 10, 2018

(65) Prior Publication Data

US 2018/0311272 A1 Nov. 1, 2018

Related U.S. Application Data

(63) Continuation of application No. 14/287,809, filed on May 27, 2014, now abandoned, which is a continuation of application No. 13/750,148, filed on Jan. 25, 2013, now abandoned, which is a continuation of application No. 12/979,981, filed on Dec. 28, 2010, now Pat. No. 8,398,611.

(51) Int. Cl.
| *A61K 31/728* | (2006.01) |
| *A61K 31/737* | (2006.01) |
| *A61M 5/19* | (2006.01) |
| *A61M 5/20* | (2006.01) |
| *A61K 9/00* | (2006.01) |
| *A61K 31/7008* | (2006.01) |

(52) U.S. Cl.
CPC .......... *A61K 31/728* (2013.01); *A61K 9/0019* (2013.01); *A61K 31/7008* (2013.01); *A61K 31/737* (2013.01); *A61M 5/19* (2013.01); *A61M 5/2066* (2013.01)

(58) Field of Classification Search
None
See application file for complete search history.

(56) References Cited

U.S. PATENT DOCUMENTS

| 3,107,605 | A | 10/1963 | Aldrich et al. |
| 3,454,560 | A | 7/1969 | Nagasawa |
| 3,697,652 | A | 10/1972 | Rovati et al. |
| 4,141,973 | A | 2/1979 | Balazs |
| 4,666,897 | A | 5/1987 | Golub et al. |
| 5,011,691 | A | 4/1991 | Oppermann et al. |
| 5,143,724 | A | 9/1992 | Leshchiner et al. |
| 5,171,579 | A | 12/1992 | Ron et al. |
| 5,258,371 | A | 11/1993 | Golub et al. |
| 5,266,683 | A | 11/1993 | Oppermann et al. |
| 5,273,056 | A | 12/1993 | McLaughlin et al. |
| 5,364,845 | A | 11/1994 | Henderson |
| 5,366,964 | A | 11/1994 | Lindstrom et al. |
| 5,380,716 | A | 1/1995 | Conrad et al. |
| 5,399,351 | A | 3/1995 | Leshchiner et al. |
| 5,409,904 | A | 4/1995 | Hecht et al. |
| 5,498,606 | A | 3/1996 | Soll et al. |
| 5,510,121 | A | 4/1996 | Rhee et al. |
| 5,789,395 | A | 8/1998 | Amin et al. |
| 5,792,103 | A * | 8/1998 | Schwartz .............. A61F 9/0017 128/898 |
| 5,814,621 | A | 9/1998 | Kanaya et al. |
| 6,030,635 | A | 2/2000 | Gertzman et al. |
| 6,051,560 | A | 4/2000 | Chang et al. |
| 6,069,135 | A | 5/2000 | Falk et al. |
| 6,197,326 | B1 | 3/2001 | Suzuki et al. |
| 6,238,372 | B1 | 5/2001 | Zinger et al. |
| 6,281,195 | B1 | 8/2001 | Rueger et al. |
| 6,288,043 | B1 | 9/2001 | Spiro et al. |
| 6,346,519 | B1 | 2/2002 | Petrus |
| 6,410,044 | B1 | 6/2002 | Chudzik et al. |
| 6,428,804 | B1 | 8/2002 | Suzuki et al. |
| 6,437,018 | B1 | 8/2002 | Gertzman et al. |
| 6,458,375 | B1 | 10/2002 | Gertzman et al. |
| 6,551,801 | B1 | 4/2003 | Andou et al. |

(Continued)

FOREIGN PATENT DOCUMENTS

| CN | 101065106 A | 10/2007 | |
| CN | 101112378 A | 1/2008 | |
| CN | 100594029 C | 3/2010 | |
| DE | 202007011252 U1 | 12/2007 | |
| EP | 0517970 A1 | 12/1992 | |
| EP | 0640647 * | 8/1994 | ............... C08L 5/08 |
| EP | 1005874 A1 | 6/2000 | |
| EP | 2033689 A1 | 3/2009 | |
| EP | 2251359 A1 | 11/2010 | |
| FR | 2866571 A1 | 8/2005 | |
| JP | 5452194 U | 4/1979 | |
| JP | H09208476 A | 8/1997 | |

(Continued)

OTHER PUBLICATIONS

Definition of "valve" downloaded from dictionarly.com Dec. 9, 2019 (Year: 2019).*

(Continued)

*Primary Examiner* — Eric Olson

(57) ABSTRACT

Compositions and methods are provided for treating joint conditions, such as osteoarthritis and/or the pain associated therewith. The compositions and methods utilize a first component, namely hyaluronic acid ("HA"), in combination with a lyophilized second component that is effective to at least temporarily reduce the viscosity of the HA. In an exemplary embodiment, the second component is one or more glycosaminoglycans ("GAG"), such as chondroitin sulfate ("CS"), including CS4 and/or CS6, dermatan sulfate, heparin, heparan sulfate, and keratan sulfate. The composition can optionally include other joint supplements, such as glucosamine ("GlcN").

21 Claims, 1 Drawing Sheet

(56) References Cited

U.S. PATENT DOCUMENTS

| | | | |
|---|---|---|---|
| 6,586,406 B2 | 7/2003 | Heidaran et al. |
| 6,608,043 B1 | 8/2003 | Serizawa et al. |
| 6,656,925 B2 | 12/2003 | Petrus |
| 6,677,321 B1 | 1/2004 | Levin |
| 6,699,471 B2 | 3/2004 | Radice et al. |
| RE38,522 E | 5/2004 | Gertzman et al. |
| 6,756,358 B2 | 6/2004 | Iwamoto et al. |
| 6,818,629 B2 | 11/2004 | Peterson et al. |
| 6,835,377 B2 | 12/2004 | Goldberg et al. |
| 6,906,044 B2 | 6/2005 | Hermida Ochoa |
| 6,911,212 B2 | 6/2005 | Gertzman et al. |
| 6,924,273 B2 | 8/2005 | Pierce |
| 6,924,370 B2 | 8/2005 | Chudzik et al. |
| 6,949,525 B2 | 9/2005 | Hermida |
| 6,972,321 B1 | 12/2005 | Hotten et al. |
| 6,979,679 B2 | 12/2005 | Marcum |
| 7,019,192 B2 | 3/2006 | Gertzman et al. |
| 7,025,959 B1 | 4/2006 | Hotten et al. |
| 7,026,292 B1 | 4/2006 | Lee et al. |
| 7,045,141 B2 | 5/2006 | Merboth et al. |
| 7,067,144 B2 | 6/2006 | Demopulos et al. |
| 7,070,942 B2 | 7/2006 | Heidaran et al. |
| 7,112,578 B2 | 9/2006 | Levin |
| 7,141,545 B2 | 11/2006 | Pike et al. |
| 7,189,392 B1 | 3/2007 | Kim et al. |
| RE39,587 E | 4/2007 | Gertzman et al. |
| 7,214,667 B2 | 5/2007 | Fukuda et al. |
| 7,223,744 B2 | 5/2007 | Yerxa et al. |
| 7,239,908 B1 | 7/2007 | Alexander et al. |
| 7,268,114 B2 | 9/2007 | Makishima et al. |
| 7,314,636 B2 | 1/2008 | Caseres et al. |
| 7,323,445 B2 | 1/2008 | Zhang et al. |
| 7,351,798 B2 | 4/2008 | Margolin et al. |
| 7,378,115 B2 | 5/2008 | Seipel |
| 7,425,573 B2 | 9/2008 | Pelletier et al. |
| 7,435,432 B2 | 10/2008 | Olson |
| 7,485,629 B2 | 2/2009 | Marcum |
| 7,582,311 B1 | 9/2009 | Cleland et al. |
| 7,592,009 B2 | 9/2009 | Hubbell et al. |
| 7,608,580 B2 | 10/2009 | Kim et al. |
| 7,651,682 B2 | 1/2010 | Devore et al. |
| 7,651,703 B2 | 1/2010 | Cleland et al. |
| 7,763,116 B2 | 7/2010 | Carter et al. |
| 7,931,030 B2 | 4/2011 | Bailleul |
| 8,398,611 B2 | 3/2013 | Hwang et al. |
| 8,623,839 B2 | 1/2014 | Su et al. |
| 9,682,099 B2 | 6/2017 | Story et al. |
| 2003/0031697 A1 | 2/2003 | Chudzik et al. |
| 2003/0086899 A1 | 5/2003 | Jafari |
| 2003/0181371 A1 | 9/2003 | Hunter et al. |
| 2003/0223983 A1 | 12/2003 | Sofia et al. |
| 2004/0038929 A1 | 2/2004 | Fukuda et al. |
| 2004/0082540 A1 | 4/2004 | Hermida Ochoa |
| 2004/0127402 A1 | 7/2004 | Vad |
| 2004/0147466 A1 | 7/2004 | Barman et al. |
| 2004/0214793 A1 | 10/2004 | Hermida Ochoa |
| 2004/0241248 A1 | 12/2004 | Margalit et al. |
| 2005/0025765 A1 | 2/2005 | DiMauro et al. |
| 2005/0079590 A1 | 4/2005 | Saha |
| 2005/0100538 A1 | 5/2005 | Mohamed et al. |
| 2005/0112186 A1 | 5/2005 | Devore et al. |
| 2005/0232981 A1 | 10/2005 | Ben-Sasson |
| 2005/0250737 A1 | 11/2005 | Hughes et al. |
| 2006/0040894 A1 | 2/2006 | Hunter et al. |
| 2006/0073207 A1 | 4/2006 | Masters et al. |
| 2006/0110459 A1 | 5/2006 | Jafari et al. |
| 2006/0122147 A1 | 6/2006 | Wohlrab |
| 2006/0122150 A1 | 6/2006 | Argentieri et al. |
| 2006/0210552 A1 | 9/2006 | Demopulos et al. |
| 2007/0053987 A1 | 3/2007 | Bayer et al. |
| 2007/0149441 A1 | 6/2007 | Aeschlimann et al. |
| 2007/0172517 A1 | 7/2007 | Ben-Sasson et al. |
| 2007/0190149 A1 | 8/2007 | Zahos |
| 2007/0203095 A1 | 8/2007 | Sadozai et al. |
| 2007/0275055 A1 | 11/2007 | Ben-Sasson et al. |
| 2007/0286881 A1 | 12/2007 | Burkinshsw |
| 2008/0003257 A1 | 1/2008 | Marcum et al. |
| 2008/0118523 A1 | 5/2008 | Hubbell et al. |
| 2008/0145404 A1 | 6/2008 | Hill et al. |
| 2008/0147065 A1 | 6/2008 | McKay et al. |
| 2008/0147077 A1 | 6/2008 | Garigapati et al. |
| 2008/0167235 A1 | 7/2008 | Zhang et al. |
| 2009/0017091 A1 | 1/2009 | Daniloff et al. |
| 2009/0017093 A1 | 1/2009 | Springer et al. |
| 2009/0035315 A1 | 2/2009 | Christgau et al. |
| 2009/0087503 A1 | 4/2009 | Henderson et al. |
| 2009/0099089 A1 | 4/2009 | Zhang et al. |
| 2009/0104148 A1 | 4/2009 | Jay et al. |
| 2009/0118348 A1 | 5/2009 | Miyamoto et al. |
| 2009/0123547 A1 | 5/2009 | Hill et al. |
| 2009/0124552 A1 | 5/2009 | Hill et al. |
| 2009/0136576 A1 | 5/2009 | Calvosa et al. |
| 2009/0162351 A1 | 6/2009 | Brown et al. |
| 2009/0162376 A1 | 6/2009 | Brown et al. |
| 2009/0181007 A1 | 7/2009 | Gennero et al. |
| 2009/0181058 A1 | 7/2009 | Li et al. |
| 2009/0202430 A1 | 8/2009 | Hoemann et al. |
| 2009/0202642 A1 | 8/2009 | Huang et al. |
| 2009/0291112 A1 | 11/2009 | Truncale et al. |
| 2010/0217231 A1 | 8/2010 | Ilan et al. |
| 2012/0165257 A1 | 6/2012 | Byers et al. |
| 2012/0165731 A1 | 6/2012 | Byers et al. |
| 2012/0165787 A1 | 6/2012 | Hwang et al. |
| 2013/0005681 A1 | 1/2013 | Su et al. |
| 2013/0172255 A1 | 7/2013 | Byers et al. |
| 2013/0178827 A1 | 7/2013 | Hwang et al. |
| 2014/0066389 A1 | 3/2014 | Eek |
| 2014/0088038 A1 | 3/2014 | Su et al. |
| 2014/0343012 A1 | 11/2014 | Hwang et al. |
| 2015/0190469 A1 | 7/2015 | Byers et al. |
| 2016/0206649 A1 | 7/2016 | Story et al. |
| 2017/0266221 A1 | 9/2017 | Story et al. |

FOREIGN PATENT DOCUMENTS

| | | |
|---|---|---|
| JP | 11302197 A | 11/1999 |
| JP | 2000212204 A | 8/2000 |
| JP | 2003501381 A | 1/2003 |
| JP | 2003160464 A | 6/2003 |
| JP | 2004359629 A | 12/2004 |
| JP | 2005-516027 A | 6/2005 |
| JP | 3748970 B2 | 2/2006 |
| JP | 2010530896 A | 9/2010 |
| JP | 2010540066 A | 12/2010 |
| KR | 20080024426 A | 3/2008 |
| WO | WO-9428889 A1 | 12/1994 |
| WO | WO-9621030 A1 | 7/1996 |
| WO | WO-9724374 A1 | 7/1997 |
| WO | WO-9728788 A1 | 8/1997 |
| WO | WO-98022114 A1 | 5/1998 |
| WO | WO-99040926 A1 | 8/1999 |
| WO | WO-03017826 A2 | 3/2003 |
| WO | WO-03034993 A2 | 5/2003 |
| WO | WO-03043660 A2 | 5/2003 |
| WO | WO-04032943 A1 | 4/2004 |
| WO | WO-05110439 A2 | 11/2005 |
| WO | WO-08098019 A2 | 8/2008 |
| WO | WO-09005790 A2 | 1/2009 |
| WO | WO-09024670 A2 | 2/2009 |
| WO | WO-09132228 A1 | 10/2009 |
| WO | WO-11086458 A1 | 7/2011 |

OTHER PUBLICATIONS

Product information for Arthrum HCS, revised Sep. 2010 (Year: 2010).*

U.S. Appl. No. 12/979,972, filed Dec. 28, 2010, Compositions and Methods for Treating Joints.

U.S. Appl. No. 12/979,981, filed Dec. 28, 2010, Compositions and Methods for Treating Joints.

U.S. Appl. No. 12/979,990, filed Dec. 28, 2010, Compositions and Methods for Treating Joints.

(56) References Cited

OTHER PUBLICATIONS

U.S. Appl. No. 13/173,658, filed Jun. 30, 2011, Compositions and Methods for Stabilized Polysaccharide Formulations.
U.S. Appl. No. 13/750,148, filed Jan. 25, 2013, Compositions and Methods for Treating Joints.
U.S. Appl. No. 13/788,838, filed Mar. 7, 2013, Methods for Forming Compositions for Treating Joints Comprising Bone Morphogenetic Protein and Hyaluronic Acid.
U.S. Appl. No. 14/090,599, filed Nov. 26, 2013, Compositions and Methods for Stabilized Polysaccharide Formulations.
U.S. Appl. No. 14/287,809, filed May 27, 2014, Compositions and Methods for Treating Joints.
U.S. Appl. No. 14/559,319, filed Dec. 3, 2014, Compositions for Treating Joints Comprising Bone Morphogenetic Protein and Hyaluronic Acid.
U.S. Appl. No. 14/600,770, filed Jan. 20, 2015, Compositions and Methods for Treating Joints.
U.S. Appl. No. 15/612,267, filed Jun. 2, 2017, Compositions and Methods for Treating Joints.
"Table of Contents." *Goodman and Gilman's: The Pharmacological Basis for Therapeutics.* Gilman et al., eds. London: Macmillan Publishers. 7th ed. (1985). 4 pages.
Benaroudj et al. "Trehalose Accumulation During Cellular Stress Protects Cells and Cellular Proteins from Damage by Oxygen Radicals." J. Biol Chem. 276.26(2001):24261-24267.
Birch. "Trehaloses." Adv. Carbohydr. Chem. 18(1963):201-225.
Celeste et al. "Identification of Transforming Growth Factor β Family Members Present in Bone-Inductive Protein Purified from Bovine Bone." PNAS. 87.24(1990):9843-9847.
Chen et al. "N-Acetylglucosamine: Production and Applications." *Mar. Drugs.* 8(2010):2493-2516.
Chen et al. "Role of Trehalose Phosphate Synthase and Trehalose During Hypoxia: From Flies to Mammals." *J. Exp. Biol.* 207. Pt18(2004):3125-3129.
Cheng et al. "Osteogenic Activity of the Fourteen Types of Human Bone Morphogenetic Proteins." *J. Bone Joint Surg. Am.* 85A(2003):1544-1552.
Communication of a notice of opposition issued in European Application No. 11195499.6 dated Aug. 7, 2014.
Euflexxa® Product information sheet. May 2011, 2 pages.
Extended Search Report issued in European Application No. 11195499.6 dated Mar. 20, 2012.
Greenfield Pharmacy, 1999, pp. 1-2.
Hoelzle et al. "Increased Accumulation of Trehalose in Rhizobia Cultured under 1% Oxygen." Appl. Environ. Microbiol. 56.10(1990):3213-3215.
Honda et al. "Direct Refolding of Recombinant Human Growth Differentiation Factor 5 for Large-Scale Production Process." *J. Biosci. Bioeng.* 89.6(2000):582-589.
Lyons et al. "Vgr-1, a Mammalian Gene Related to Xenopus Vg-1, is a Member of the Transforming Growth Factor β Gene SUperfamily." PNAS. 86.12(1989):4554-4558.
Mankin et al. "The Glycosaminoglycans of Normal and Arthritic Cartilage." *J. Clin. Invest.* 50.8(1971):1712-1719.
Massaqué. "The Transforming Growth Factor-β Family." *Annu. Rev. Cell Biol.* 6(1990):597-641.
Minutoli et al. "The Disaccharide Trehalose Inhibits Proinflammatory Phenotype Activation in Macrophages and Prevents Mortality in Experiment Septic Shock." *Shock.* 27.1(2007):91-96.
Orthovisc® detailed product information. Jun. 2005, 2 pages. Retrieved Apr. 25, 2012 from <http://www.depuy.com/sites/default/files/products/files/OrthoviscNonAvianPIFinal2010.pdf>.
Orthovisc®. Manufactured by Anika Therapeutics, Inc. of Bedford, MA. Retrieved Mar. 30, 2011 from <http://www.orthovisc.com/orthvisc>, 2 pages.
Ozkaynak et al. "OP-1 cDNA Encodes an Osteogenic Protein in the TGF-β Family." *EMBO J.* 9.7(1990):2085-2093.
Partial Search Report issued in European Application No. 12174614.3 dated Aug. 14, 2012.

*Pharmaceutics: The Science of Dosage Form Design*. Aulton, ed. London: Churchill Livingston. 2nd ed. (2002):390-393.
*Remington's Pharmaceutical Sciences.* Easton, PA: Mack Publishing Co. 15th ed. (1975):1405-1412, 1461-1487.
Rohanizadeh et al. Hydroxyapatite as a Carrier for Bone Morphogenetic Protein. J. Oral Implantol. 37.6(2011):659-672.
Ruppert et al. "Human Bone Morphogenetic Protein 2 Contains a Heparin-Binding Site which Modifies its Biological Activity." Eur. J. Biochem. 237.1(1996):295-302.
Sampath et al. "Bovine Osteogenic Protein is Composed of Dimers of OP-1 and BMP-2A, Two Members of the Transforming Growth Factor-b Superfamily." J. Biol. Chem. 265.22(1990):13198-13205.
Shiseido. Sodium Hyaluronate. Medical Grade.1993, 4 pages.
The National Formulary XIV., 14th ed. Washington: American Pharmaceutical Association, 1975.
United Sugars Corporation, 2010, p. 1.
Wharton et al. "*Drosophila* 60A Gene, Another Transforming Growth Factor b Family Member, is Closely Related to Human Bone Morphogenetic Proteins." PNAS. 88.20(1991):9214-9218.
Yoshizane et al. "Trehalose Suppresses Osteoclast Differentiation in Ovariectomized Mice: Correlation with Decreased in vitro Interleukin-6 Production by Bone Marrow Cells." Nutr. Res. 20.10(2000):1485-1491.
Indian Examination Report dated Aug. 13, 2015 for Application No. 3778/DEL/2011 (3 Pages).
Vejlens L. "Glycosaminoglycans of human bone tissue." I. Pattern of compact bone in relation to age. Calcif Tissue Res. 1971;7(2):175-90.
Barbucci et al., Hyaluronic acid hydrogel in the treatment of osteoarthritis. Biomaterials. Dec. 2002;23(23):4503-13.
Japanese Office Action dated Dec. 8, 2015 for Application No. 2011-285276 (English translation).
European Search Report for Application No. EP 16151940.0, dated Jul. 7, 2016.
Maleki et al., Effect of pH on the behavior of hyaluronic acid in dilute and semidilute aqueous solutions. Macromolecular Symposia. Dec. 1, 2008;247(1)131-140.
Liang et al. The relationship between low pH in intervertebral discs and low back pain: a systematic review. Arch Med Sci. Dec. 20, 2012;8(6):952-6.
Rabago et al., Hypertonic dextrose injections (prolotherapy) for knee osteoarthritis: results of a single-arm uncontrolled study with 1-year follow-up. J Altern Complement Med. Apr. 2012;18(4):408-14.
Office Action for Chinese Application No. 201210223133.6, dated Jul. 25, 2016.
Chinese Office Action dated Sep. 26, 2016 for Application No. 201410211992.2.
Japanese Office Action for Application No. 2016-175315, dated Jul. 18, 2017.
European Search Report for Application No. 17185327.8 dated Nov. 16, 2017.
Ko et al., Type II collagen-chondroitin sulfate-hyaluronan scaffold cross-linked by genipin for cartilage tissue engineering. J Biosci Bioeng. Feb. 2009;107(2):177-82.
Tokita et al., Degragation of hyaluronic acid during freeze drying. Polymer Degradation and Stability. 1997;55(2):159-64.
Michaels et al., "Dual Chamber Prefill Syringes" PDA Journal of Pharmaceutical Science and Technology col. 2 No. 6 pp. 199-202 (Year: 1988).
Frisbie et al., "Evaluation of intra-articular hyaluronan, sodium chondroitin sulfate and N-acetyl-o-glucosamine combination versus saline (0.9% NaCl) for osteoarthritis using an equine model." The Veterinary Journal, vol. 197 (2013): 324-829.
POLYGLYCAN Product Information. IC Bimeda. www.BimedaUS. com, Sep. 2017 (3 pages).
POLYGLYCAN®-HV Product Information. IC Bimeda. www. BimedaUS.com, Sep. 2017 (3 pages).
POLYGLYCAN®-SA Product Information. IC Bimeda. www. BimedaUS.com, Sep. 2017 (3 pages).
ORTHOVISC Product Information. DePuy Synthes, Mitek Sports Medicine, DePuy Mitek, Inc., www.depuysynthes.com, Sep. 2014, (9 pages).

(56) References Cited

OTHER PUBLICATIONS

Hu, R. (Ed.) Industrial Pharmaceutics, China Herbal Medicine Press, Aug. 31, 2010, pp. 426-434.
Chen, J. (Ed.), "365 questions in prevention and treatment of common rheumatism," May 31, 2013. pp. 253-255.
Wang, R. (Ed.), Pharmaceutics, People's Hygiene Press, Oct. 31, 2000, pp. 255-260.
Translation of Chinese Search Report for CN Application 201610037012 dated Sep. 26, 2019 (2 pages).

* cited by examiner

COMPOSITIONS AND METHODS FOR TREATING JOINTS

CROSS REFERENCE TO RELATED APPLICATIONS

This application is a continuation of U.S. patent application Ser. No. 14/287,809 filed on May 27, 2014 and entitled "Compositions and Methods for Treating Joints," which is a continuation of U.S. patent application Ser. No. 13/750,148 filed on Jan. 25, 2013, now abandoned, and entitled "Compositions and Methods for Treating Joints," which is a continuation of U.S. patent application Ser. No. 12/979,981 filed on Dec. 28, 2010 and entitled "Compositions and Methods for Treating Joints," and which issued as U.S. Pat. No. 8,398,611 on Mar. 19, 2013, each of which is hereby incorporated by reference in its entirety.

FIELD OF THE INVENTION

The present invention relates generally to compositions and methods for treating joints.

BACKGROUND OF THE INVENTION

Osteoarthritis ("OA"), the most common form of arthritis, is a type of arthritis that is characterized by degenerative (gradual deterioration of joint) or abnormal changes in bone, cartilage, and synovium of the joints. OA is often characterized by a progressive wearing down of opposing joint surfaces accompanied at times by inflammation resulting in pain, swelling, and stiffness for the patient. OA can occur in one or more joints following trauma to the joint, following an infection of the joint, or simply as a result of aging. Furthermore, there is emerging evidence that abnormal anatomy may contribute to early development of OA.

Treatment of OA generally involves a combination of exercise or physical therapy, lifestyle modification, and analgesics. Acetaminophen is typically the first line treatment for OA. For mild to moderate symptoms, effectiveness is similar to non-steroidal anti-inflammatory drugs ("NSAIDs"), such as ibuprofen. For more severe symptoms NSAIDs may be more effective. However, while more effective, NSAIDs in severe cases are associated with greater side effects such as gastrointestinal bleeding and renal complications. Another class of NSAIDs, COX-2 selective inhibitors (such as Celecoxib), are equally effective to NSAIDs but no safer in terms of side effects. There are several NSAIDs available for topical use including diclofenac. Typically, they have less systemic side-effects than oral administration and at least some therapeutic effect. While opioid analgesic, such as morphine and fentanyl, improve pain this benefit is outweighed by frequent adverse events and thus they are not routinely used. Intra-articular steroid injections are also used in the treatment of OA and they are very effective at providing pain relief. However, the durability of the pain relief is limited to 4-6 weeks and there are adverse effects that may include collateral cartilage damage. If pain becomes debilitating, joint replacement surgery may be used to improve mobility and quality of life. There is no proven treatment to slow or reverse the disease.

For patients who do not get adequate pain relief from simple pain relievers, like acetaminophen or from exercise and physical therapy, intra-articular injections of hyaluronic acid (HA) provide another treatment option to address symptomatic pain and delay the need for a total joint replacement surgery. It is known that the concentration of native HA is deficient in individuals suffering from OA and therefore joint injections of exogenous HA is believed to replenish these molecules and restore the viscoelastic properties of synovial fluid. It is this property that is responsible for lubricating and cushioning the joints. There is also evidence that HA has biological activity through binding to cell surface receptors and may have a role in mitigating inflammation. Independent of the mechanism of action, pain relief is observed for about six months following a treatment course. A treatment course for HA products on the US market can range from single injection product to others that require 3 to 5 weekly injections to attain this durability of pain relief.

There remains a need for improved methods and compositions for treating OA joints, and in particular to improved methods and compositions for treating joints using HA combined with one or more GAGs to address the pain and structural degeneration associated with OA.

SUMMARY OF THE INVENTION

The present invention generally provides compositions and methods for treating joint conditions, such as osteoarthritis and/or the pain associated therewith. In one embodiment, a kit for treating joints is provided and includes a first component comprising hyaluronic acid ("HA"), a second component comprising a lyophilized glycosaminoglycan ("GAG"), and a syringe for injecting a mixture of the first and second components. While various GAGs can be used, in one embodiment the GAG comprises chondroitin sulfate. The kit can also include a third component, such as glucosamine, which in some embodiments can be lyophilized.

The composition of the components can vary. In one embodiment, when the first and second components are combined to form a mixture, the first and second components are present within the mixture at a ratio of first component to second component in the range of about 1:0.005 to 1:100 by weight. In other aspects, the hyaluronic acid can be lyophilized. In one exemplary embodiment, the hyaluronic acid has a molecular weight in the range of about 1 million Daltons (MDa) to 4 MDa, and a concentration of at least about 5 mg/ml, and more preferably at least about 7 mg/ml. The kit can also include a third component comprising a fluid that is effective to solubilize the first and second components. The fluid can be, for example, water, saline, and/or a buffer.

The syringe can have various configurations, and in one embodiment the syringe has a first chamber containing the first component, a second container containing the second component, and a plunger configured to inject the second component into the first chamber to mix the first and second components. In another embodiment, the second component can be disposed within a container, and the syringe can include a first chamber containing the first component and a connector for removably coupling the container to the syringe such that a plunger slidably disposed within the first chamber of the syringe can inject the first component into the container to mix the first and second components.

In other aspects, a method for treating joints is provided and includes combining a first component comprising hyaluronic acid with a second component comprising a lyophilized glycosaminoglycan to form a mixture, and injecting the mixture into a joint. The glycosaminoglycan can be, for example, chondroitin sulfate. The kit can also include a third component, such as glucosamine. In certain aspects, the glucosamine, if present, can be lyophilized. When the components are combined, a viscosity of the mixture is less than a viscosity of the hyaluronic acid prior to combining. In another embodiment, the hyaluronic acid is lyophilized, and the first and second components are solubilized prior to or during combining the first and second components to form a mixture. The first and second components can be combined, for example, in a vial and drawn into a syringe, which can be used to inject the mixture into a joint. In an exemplary embodiment, the first and second components are drawn into the syringe after forming the mixture, for example within about 30 minutes of formation of the mixture. In another embodiment, the first component is disposed within a first chamber in a syringe, and the second component is disposed within a second chamber in the syringe, and combining the first and second components comprises injecting the first component into the second chamber. In yet another embodiment, combining the first and second components comprises coupling a container having the first component disposed therein to a syringe having the second component disposed therein, and injecting the second component from the syringe into the container.

The first component can have various concentrations and molecular weights, but in one embodiment the concentration is at least about 5 mg/ml, and more preferably at least about 7 mg/ml and the molecular weight is in the range of about 1 MDa to 4 MDa. In an exemplary embodiment, the first and second components are present within the mixture at a ratio of about 1:0.005 to 1:100.

BRIEF DESCRIPTION OF THE DRAWINGS

The appended drawings have been included herein so that the above-recited features, advantages and objects will become clear and can be understood in detail. These drawings form a part of the specification. It is to be noted, however, that the appended drawings illustrate exemplary embodiments and should not be considered to limit the scope.

DETAILED DESCRIPTION OF THE INVENTION

Figure 1:
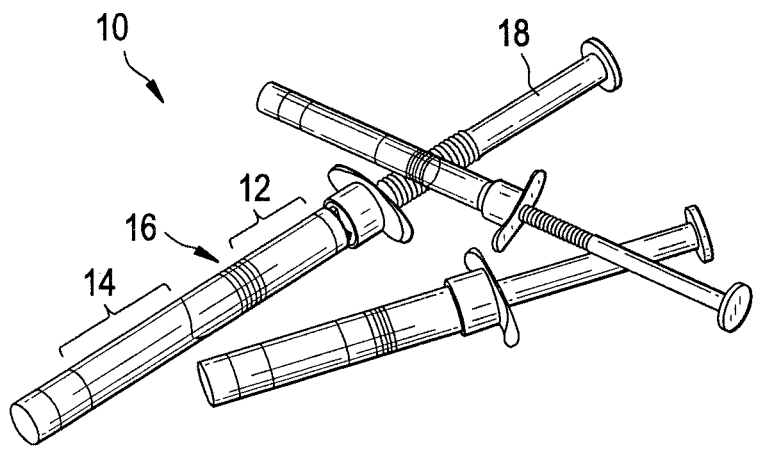
FIG. 1 is a perspective view of one embodiment of a mixing and delivery system for use with the compositions and methods of the present invention.

In general, the present invention provides compositions and methods for treating joint conditions, such as osteoarthritis and/or the pain associated therewith. The compositions and methods utilize a first component, namely hyaluronic acid ("HA"), in combination with a lyophilized second component that is effective to at least temporarily reduce the viscosity of the HA. In an exemplary embodiment, the second component is one or more glycosaminoglycans ("GAG"), such as chondroitin sulfate ("CS"), including CS4 and/or CS6, dermatan sulfate, heparin, heparan sulfate, and keratan sulfate. The composition can optionally include other joint supplements, such as glucosamine ("GlcN").

It has been discovered that the use of a lyophilized GAG has the effect of at least temporarily reducing the viscosity of HA such that a composition formed from lyophilized GAG and HA has a viscosity that is (at least temporarily) significantly less than the viscosity of the HA alone. While it is desirable to use HA at high molecular weights and high concentrations, the viscosity of HA significantly increases as the molecular weight and concentration increases. As a result, HA is typically either used at low molecular weights and concentrations to allow for intra-operative mixing, or HA is mixed during manufacture. Mixing the HA in advance of the time of its intended use, such as at the time of manufacture, can present issues with respect to the stability and shelf life of the HA composition. The discovery that lyophilized GAG is effective to reduce the viscosity of the HA, at least temporarily, enables the use of HA at high molecular weights and concentrations, thus allowing it to be mixed with GAG intra-operatively, i.e., immediately prior to or during surgery, and thereby eliminating any composition stability and shelf life issues. This decrease in viscosity is sufficient to allow mixing to take place without the use of any mechanical aid, such as a vortexer, mixer, or a spatula. Therefore, there is need for specific instruments or stirrers that could compromise sterility to create a formulation that combines HA and CS.

First Component

The first component, HA, can have various formulations and can be provided at various concentrations and molecular weights. The terms "hyaluronic acid," "hyaluronan," and "HA" are used interchangeably herein to refer to hyaluronic acids or salts of hyaluronic acid, such as the sodium, potassium, magnesium, and calcium salts, among others. These terms are also intended to include not only elemental hyaluronic acid, but hyaluronic acid with other trace elements or in various compositions with other elements. The terms "hyaluronic acid," "hyaluronan," and "HA" encompass chemical or polymeric or cross-linked derivatives of HA. Examples of chemical modifications which may be made to HA include any reaction of an agent with the four reactive groups of HA, namely the acetamido, carboxyl, hydroxyl, and the reducing end. The HA used in the present application is intended to include natural formulations, synthetic formulations, or combinations thereof. The HA can be provided in liquid or solid formulations, and the HA can be in pure liquid form or in a solvent at various concentrations.

HA is a glycosaminoglycan (GAG), and in particular HA is an unbranched polysaccharide made up of alternating glucuronic acid and N-acetyl glucosamine units. It is a viscoelastic material that is also found in the extracellular matrix of cartilage attached to collagen. In particular, HA is an important building component of aggregated proteoglycans which impart resilient characteristics of articular cartilage. HA not only helps keep the cartilage that cushions joints strong and flexible, but it also helps increase supplies of joint-lubricating synovial fluid. HA abnormalities are a common thread in connective tissue disorders. HA can thus be used, to prevent, treat, or aid in the surgical repair of connective tissue disorders.

HA can be used in the compositions and methods of the present invention at various molecular weights. Since HA is a polymeric molecule, the HA component can exhibit a range of molecular weights, and almost any average of modal molecular weight formulation of HA can be used in the compositions and methods of the present invention, including Low Molecular Weight ("LWM") Hyaluronan (about 500 to 700 kilodaltons (kDa) Medium Molecular Weight ("MMW") Hyaluronan (700-1000 kDa), and High Molecular Weight ("HMW") Hyaluronan (1.0-4.0 million daltons (MDa)). In certain exemplary embodiments, the HA has a molecular weight of at least about 500 kDa, and more preferably the HA is a High Molecular Weight ("HWM") HA having a molecular weight of at least about 1 MDa. The molecular weight can be, for example, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000 kDa or more, or any range derivable therein. It is expected that chemically modified HA's could have very different molecular weights than described above. A crosslinked HA can have much higher molecular weight than noted above. Regardless, these materials are also applicable in this invention preferably when combined with a non-crosslinked or lightly crosslinked HA in the formulation.

The concentration of HA present in mixture can also vary, but in an exemplary embodiment HA is provided at a pharmaceutically effective amount. In an exemplary embodiment, the HA has a concentration of at least about 5 mg/ml, and more preferably at least about 7 mg/ml, and more preferably at least about 10 mg/ml, and more preferably at least about 15 mg/ml, and in some embodiments the concentration can be at least about 20 mg/ml. Suitable concentrations of HA include about 5 mg/ml, 6 mg/ml, 7 mg/ml, 8 mg/ml, 9 mg/ml, 10 mg/ml, 11 mg/mg, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59 mg/ml, 60 mg/ml or more or any range derivable therein.

In one embodiment, the first component comprises an HA having a high molecular weight (e.g., 1 to 4 MDa) and a concentration in the range of about 7-40 mg/ml. One such product is Orthovisc® manufactured by Anika Therapeutics, Inc. of Bedford, Mass. Orthovisc® is a sterile, non-pyrogenic, clear, viscoelastic solution of hyaluronan. Orthovisc® consists of high molecular weight (1.0-2.9 MDa), ultra-pure natural hyaluronan dissolved in physiological saline and having a nominal concentration of 15 mg/ml. Orthovisc® is isolated through bacterial fermentation. A person skilled in the art will appreciate that HMW HA can be obtained from a number of sources, such as Shiseido and Lifecore. Another example of an HA product in the US with these characteristics is Euflexxa®.

Second Component

The second component used in the methods and compositions of the present invention can also have a variety of configurations, but in an exemplary embodiment the second component is a lyophilized glycosaminoglycan (GAG). The term "glycosaminoglycan," or "GAG," refers interchangeably to the family of sulfated mucopolysaccharides that typically include heparin, heparin sulfate, chondroitin, chondroitin sulfate, keratan sulfate, dermatan sulfate, and their respective derivatives.

Glycosaminoglycans (GAGs) are long unbranched polysaccharides containing a repeating disaccharide unit. The disaccharide units contain either of two modified sugars, N-acetylgalactosamine (GalNAc) or N-acetylglucosamine (GlcNAc), and a uronic acid such as glucuronate or iduronate. GAGs are highly negatively charged molecules, with extended conformation that imparts high viscosity to the mixture. GAGs are located primarily on the surface of cells or in the extracellular matrix (ECM). Along with the high viscosity of GAGs comes low compressibility, which makes these molecules ideal for a lubricating fluid in the joints. GAGs can thus help slow down the inflammatory process. At the same time, their rigidity provides structural integrity to cells and provides passageways between cells, allowing for cell migration. In addition, a GAG such as CS has been found in the synovial fluid and may play a role in health of the joint. Therefore it makes sense to have a therapy that can deliver CS at the same time as HA. It is believed that CS can enhance the efficacy of HA. However, we have observed that HA in the presence of CS can degrade over time. Therefore, in order to prevent this degradation from taking place, it needs to be stored refrigerated until use. However, we know that most clinics and hospital do not have the capacity to store these types of products in a refrigerator therefore we needed to find a way to provide products that can combine HA and GAG while maintaining the ability to keep them at room temperature.

One way to increase stability of a formulation is to provide the product as a lyophilized product that can be resuspended with a diluent just prior to or at the time of injection. For example, a lyophilized GAG can be provided for resuspending with an HA gel just prior to or at the time of injection. Unfortunately, HA's at high molecular weights and/or high concentrations are extremely viscous. Even with this high viscosity, surgeons are able to deliver the formulation into the joint because HA, especially uncrosslinked HA's, have lower viscosity with increasing shear rate. This phenomenon, called shear thinning, occurs when the HA is pushed through a needle. The HA shear thins or the viscosity decreases which helps to facilitate the injection into that patient's joint. When the HA is not under a mechanical force, the viscosity remains high and makes it difficult to be able to dissolve and mix another active into the HA without any mechanical aid or mixing system.

It has been discovered that when HA is combined with GAGs, and in particular lyophilized GAGs, the GAG, once dissolved, can at least temporarily reduce the viscosity of HA sufficiently to allow mixing to take place. The advantage of a lyophilized GAG formulation over a liquid GAG formulation is that it allows the HA component to be used at higher concentrations. While a liquid GAG can be combined with HA, such a mixture of liquid GAG and HA would yield a lower concentration of HA. It is believed that higher concentrations of HA's are desirable to provide durability of pain relief in the clinical setting. While various GAGs can be used, in certain exemplary embodiments the lyophilized GAG is sulfated, and more particularly it is one or more of chondroitin sulfate (CS), including CS4 and/or CS6, dermatan sulfate, heparin, heparan sulfate, and keratan sulfate.

The GAGs can have various molecular weights, but in certain exemplary embodiments the molecular weight is in the range about 5 to 1,000 kDa, more preferably in the range of about 6 to 500 kDa, more preferably in the range of about 7 to 300 kDa, more preferably in the range of about 8 to 200 kDa, more preferably in the range of about 9 to 100 kDa, and most preferably in the range of about 10 to 80 kDa. In other embodiments, the molecular weight of the GAG fragment is below about 5 kDa and even more preferably below about 3 kDa.

The concentration of GAGs present in mixture can also vary, but in an exemplary embodiment the GAG is provided at a pharmaceutically effective amount. In an exemplary embodiment, the GAG has a concentration of at least about 0.1 mg/ml, and more preferably at least about 2 mg/ml, and more preferably at least about 5 mg/ml, and more preferably at least about 7 mg/ml. Suitable concentrations of GAGs include about 5 mg/ml, 6 mg/ml, 7 mg/ml, 8 mg/ml, 9 mg/ml, 10 mg/ml, 11 mg/mg, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59 mg/ml, 60 mg/ml or more or any range derivable therein.

Chondroitin sulfate (CS), which is an essential component of cartilage, is composed of an alternating sequence of sulfated and/or unsulfated D-glucuronic acid (GlcA) and N-acetyl-D-galactosamine (GalNAc) residues linked through alternating $\beta(1,3)$ and $\beta(1,4)$ bonds. These compounds each have a polymeric structure consisting mainly of about 40 to 100 times repetition of the disaccharide units. CS can be used at various molecular weights and concentrations, as discussed above with respect to the GAG component, but in an exemplary embodiment, the CS has a molecular weight of in the range of about 10,000 to 80,000 kDa and a concentration in the range of about 0.1 to 100 mg/ml. CS can be isolated from bovine or marine sources. A chondroitin chain can have over 100 individual sugars, each of which can be sulfated in variable positions and quantities. Chondroitin-4 sulfate, also carbon 4 of the N-acetylgalactosamine (GalNAc) sugar, is found in nasal and tracheal cartilages of bovines and porcines. It is also found in the bones, flesh, blood, skin, umbilical cord, and urine of these animals. Chondroitin-6 sulfate, also carbon 6 of the GalNAc sugar, has been isolated from the skin, umbilical cord, and cardiac valves of these animals. Chondroitin-6 sulfate has the same composition, but slightly different physical properties from chondroitin-4 sulfate. Chondroitin sulfate is involved in the binding of collagen and is also directly involved in the retention of moisture. These are both properties that aid the healing process. A person skilled in the art will appreciate that the terms "chondroitin sulfate," "CS," "chondroitin," "chondroitin sulfuric acid," and "chonsurid" are used interchangeably herein and also encompass chemical or isomeric or cross-linked derivatives throughout this application.

Dermatan sulfate (DS), also called chondroitin sulfate B, is mainly made up disulfated and/or trisulfated disaccharide units of L-iduronic acid and N-acetyl-D-galactosamine joined by $\beta1,4$ or 1,3 linkages, but there is a case where some of the repeating units contain sulfated L-iduronic acid or D-glucuronic acid as uronic acid, or contain non-sulfated N-acetylgalactosamine or 4,6-disulfated N-acetylgalactosamine instead of N-acetylgalactosamine-4-sulfate. DS is defined as a chondroitin sulfate by the presence of GalNAc. The presence of iduronic acid (IdoA) in DS distinguishes it from chondroitin sulfates-A (4-O-sulfated) and -C (6-O-sulfated) and likens it to heparin and HS, which also contain this residue. It is considered that dermatan sulfate is absorbed by the body when orally taken. The molecular weight and concentration of DS can vary, as discussed above with respect to the GAG component, but in an exemplary embodiment the molecular weight is in the range of about 10 to 80 kDa and a concentration in the range of about 0.1-100 mg/ml. A person skilled in the art will appreciate that, unlike HA which is bacterially fermented and therefore has a molecular weight that can be controlled, dermatan sulfate is isolated from animal tissue and may contain fragments. The molecular weight of the dermatan sulfate, and any fragments contained therein, can therefore significantly vary. A person skilled in the art will also appreciate that the terms "dermatan sulfate," "DS," and "dermatan" are used interchangeably herein and also include sulfated derivatives of dermatan sulfate, the dermatan sulfate benzethonium salt, the persulfated derivatives of dermatan sulfate benzethonium salts, and also the dermatan sulfate sodium salt.

Heparin and heparan sulfate (HS) are composed of a glucuronic acid (GlcA) linked to N-acetylglucosamine. They are composed of $\alpha1$-4 linked disaccharide repeating units containing a uronic acid and an amino sugar. Heparan sulfate proteoglycans are an integral part of the basement membrane. HA is a large biomolecule with a molecular mass as great as 400 kDa, composed of a core protein covalently bound to heparan sulfate chains. The number of the polysaccharide chains and the size of the core protein may vary according to the source. Heparan sulfate proteoglycan is a multifunctional molecule binding to fibroblast growth factors, vascular endothelial growth factor (VEGF), and VEGF receptors through the sugar moiety, acting as a docking molecule for matrilysin (MMP-7) and other matrix metalloproteinases and playing important roles in cell proliferation and differentiation. Heparan sulfate proteoglycans also promote attachment of cells by binding to a variety of molecules found in the extracellular matrix including laminin, fibronectin, collagen type IV, and FGF-basic. The molecular weight and concentration of HS can vary, as discussed above with respect to the GAG component, but in an exemplary embodiment the molecular weight is in the range of about 3-30 kDa (when isolated from tissues) and a concentration in the range of about 0.1-100 mg/ml.

Keratan sulfate, also keratosulfate (KS), is highly-negatively charged and found principally in aggrecan, the most abundant proteoglycan in the extracellular matrix of hyaline, fibrous and elastic cartilage. KS is composed of disaccharide repeating unit, -4GlcNAc$\beta$1-3Gal$\beta$1-. Sulfation occurs at carbon position 6 (C6) of either or both the galactose (Gal) or GlcNAc. Specific KS types are composed of three regions: alinkage region, at one end of which the KS chain is linked to the core protein, the repeating disaccharide unit, and chain capping region, occurring at the opposite end of the KS chain to the protein linkage region. The molecular weight and concentration of KS can vary, as discussed above with respect to the GAG component, but in an exemplary embodiment the molecular weight is in the range of about 5-10 kDa (when isolated from tissues) and a concentration in the range of about 1-100 mg/ml.

A person skilled in the art will appreciate that, while lyophilized GAGs are particularly preferred, liquid GAGs can also be used to at least temporarily reduce the viscosity of HA. For example, CS can be obtained in powder form and mixed with a solvent, such as water, to form a solution. The solution can be combined with HA to form a mixture having a reduced viscosity, as compared to the HA alone. While effective to reduce the viscosity of the HA, the resulting mixture will have a reduced concentration due to the presence of water. Thus, while liquid, non-lyophilized GAGs can be used with the present invention, in an exemplary embodiment the GAG is lyophilized to allow for the use of HA at a high concentration.

Lyophilization

Any one or more of the components present in the compositions and methods of the present invention can be lyophilized using various techniques known in the art. Lyophilization is a dehydration process that is typically used to preserve a perishable material, and it works by freezing the material and then reducing the surrounding pressure and adding enough heat to allow the frozen water in the material to sublime directly from the solid phase to the gas phase. Standard lyophilization techniques known in the art can be used to lyophilize any one or more of the components. In an exemplary embodiment, at a minimum the second component, namely one or more GAGs, is lyophilized.

Prior to lyophilization, various solvents can be used to form an aqueous mixture containing the component(s) to be lyophilized. In an exemplary embodiment, the aqueous mixture is prepared by combining water with one or more of the components. The component(s) can be present within the mixture at various amounts, for example in the range of about 1 to 100 mg/ml, and more preferably at about 50 mg/ml. In an exemplary embodiment, the composition is sterilized using a filter, such as a 0.2 μm filter, prior to lyophilization. One filtration technique which can be used is aseptic filtration.

In one embodiment, the component(s) can be lyophilized using the following cycle:
    Freezing: from ambient temperature to 5° C. in 15 minutes
        Hold at 5° C. for 100 minutes
        Down to −45° C. in 50 minutes
        Hold at −45° C. for 180 minutes
    Primary Drying: set pressure at 50 mTorr
        Shelf Up to −15° C. in 175 minutes
        Hold at −15° C. for 2300 minutes
    Secondary Drying: set pressure at 75 mTorr
        Shelf Up to 25° C. in 200 minutes
        Hold for 900 minutes
    Cycle end: backfill with nitrogen to ~730 Torr
        Capping and crimping The addition of a buffering agent can provide for improved solubility and stability of the GAG in lyophilized formulations. Biocompatible buffering agents known in the art can be used, such as glycine; sodium, potassium, or calcium salts of acetate; sodium, potassium, or calcium salts of citrate; sodium, potassium, or calcium salts of lactate; sodium or potassium salts of phosphate, including mono-basic phosphate, di-basic phosphate, tri-basic phosphate and mixtures thereof. The buffering agents can additionally have glycine added to the composition to function as a bulking agent.

Other Joint Supplements

The components and methods of the present invention can also include additional components or joint supplements to enhance the treatment effect. For example, glucosamine ($C_6H_{13}NO_5$) ("GlcN") can enhance synthesis of key components of synovial fluid by feeding both reactions necessary for the production of hyaluronan as well as for proteoglycans. GlcN is an amino sugar carrying four hydroxyl groups and an amine group, and it is a prominent precursor in the biochemical synthesis of glycosylated proteins and lipids. GlcN is a naturally occurring molecule that has nutritive and effector functions. For example, GlcN is compatible with and promotes stem cell growth and differentiation of mesenchymal stem cells to form chondrocytes. GlcN can have a role in tissue development and repair, such as cartilage growth and development, in general. In one embodiment, the GlcN can by lyophilized together with the CS. Salt forms of glucosamine can have limited stability in liquid phase. In addition, HCl salt of GlcN can lower the pH sufficiently to degrade the HA once combined. For this reason, in order to retain stability of the components, it is advantageous to have GlcN in the lyophilized form to be solubilized with HA gel prior to injection.

The concentration of the GlcN can vary. A suitable local concentration can be at least about 10 mg/ml, about 9 mg/ml, about 8 mg/ml, about 7 mg/ml, about 6 mg/ml, 5 mg/ml, 4.5 mg/ml, 4 mg/ml, 3.5 mg/ml, 3 mg/ml, about 2.9 mg/ml, about 2.8 mg/ml, about 2.7 mg/ml, about 2.6 mg/ml, about 2.5 mg/ml, about 2.4 mg/ml, about 2.3 mg/ml, about 2.2 mg/ml, about 2.1 mg/ml, about 2.0 mg/ml, about 1.9 mg/ml, about 1.8 mg/ml, about 1.7 mg/ml, about 1.6 mg/ml, about 1.5 mg/ml, about 1.4 mg/ml, about 1.3 mg/ml, about 1.2 mg/ml, about 1.1 mg/ml, about 1.0 mg/ml, about 0.9 mg/ml, about 0.8 mg/ml, about 0.7 mg/ml, about 0.6 mg/ml, about 0.5 mg/ml or so on. A person skilled in the art can determine a suitable local concentration of GlcN practicing methods known in the pharmaceutics art, and that determination will govern the nature and composition of the GlcN composition of interest to obtain the desired concentration of GlcN.

A person skilled in the art will appreciate that the compositions and methods of the present invention can include various other joint treatment or excipients, including, for example, amino acids, proteins, nucleic acids, buffers, surfactants and mixtures thereof. Steroids, anti-inflammatory agents, non-steroidal anti-inflammatory agents, analgesics, cells, stabilizers, antibiotics, antimicrobial agents, anti-inflammatory agents, growth factors, growth factor fragments, small-molecule wound healing stimulants, hormones, cytokines, peptides, antibodies, enzymes, isolated cells, platelets, immunosuppressants, nucleic acids, analgesics, cell types, viruses, virus particles, and combinations thereof.

Composition

The first and second components, as well as any additional components, can be combined to form a composition that is able to be injected into tissue. As indicated above, one or more of the components, and preferably at least the second component (the GAG), is lyophilized and is therefore a solid. In the event all components are lyophilized, the components can be provided in one or more containers, and then reconstituted with water, saline, buffer, or another solvent. The solubilization of a lyophilized or solid HA with a lyophilized GAG can allow for faster solubilization of HA. Where one or more of the components is a liquid, and one or more of the components is a solid, the solid component(s) can be provided in a first container or in a first chamber of a container, and the liquid component(s) can be provided in a second container or in a second chamber of a container. The solid component(s) can be solubilized by the liquid component(s) or with a diluent. Once the components are fully solubilized, the composition will at least temporarily exhibit a significantly reduced viscosity, as compared to the viscosity of HA alone, thus allowing the composition to be injected into tissue using a syringe.

In one embodiment, the second component is lyophilized and the first component is in an aqueous solution. The components are provided in separate containers or separate chambers, and just prior to or during surgery the lyophilized second component is reconstituted with the first component. In particular, HA can be provided in liquid form, and lyophilized GAG can be combined with the HA. Once fully solubilized in the HA, the viscosity of the HA will be significantly reduced, at least temporarily, allowing for mixing of the two components and ease of injection of the mixture. Alternatively, the lyophilized second component can be constituted with water, saline, or other solvent, and then combined with the HA to form an injectable mixture.

In another embodiment, the first and second components are both lyophilized and provided in solid form. The components can be provided in separate containers or chambers, or they can be provided in a single container or chamber. The components can be reconstituted with water, saline, or other solvent to form an injectable mixture. The lyophilized second component, e.g., one or more GAGs, will have the affect of reducing the viscosity of the mixture, at least temporarily.

In an exemplary embodiment, the components are configured to be combined intraoperatively, i.e., immediately before or during an operation. The components, when combined, can form a resulting ready-to-use composition or mixture having each component present in the composition at various amounts. The amount of each component in the ready-to-use composition can vary, but in an exemplary embodiment the second component, e.g., one or more GAGs, is present at an amount that is sufficient to reduce the viscosity of the first component, e.g., HA. For example, the first component, e.g., HA, and the second component, e.g., GAG, can be mixed at a ratio of the first component to the second component in the range of about 1:0.001 to 1:200, and in some embodiment of about 1:0.005 to 1:100. The resulting concentration of the first component in the ready-to-use composition can thus be in the range of about 0.6% to 4%% or more by weight of the total composition and the resulting concentration of the second component in the ready-to-use composition can thus be in the range of about 0.001% to 10%. More preferably, the first component can be present in the ready-to-use composition at a concentration of about 0.6%, 1%, 1.5%, 2%, 2.5%, 3%, 3.5%, 4% or more by weight of the total composition, and the second component can be present in the ready-to-use composition at a concentration of about 0.001%, 0.01%, 0.1%, 1%, 2%, 3%, 4%, 5%, 6%, 7%, 8%, 9%, 10% or more by weight of the total composition. In an exemplary embodiment, the amount of HA present in the disclosed compositions is about 1.5-2.5% by weight of the total composition, and the amount of GAG present in the disclosed compositions is about 0.001 to 10% by weight of the total composition.

Other solvents that can be used to solubilize one or more of the components include, for example, saline or other salt solutions, buffer solutions such as phosphate buffered saline, histidine, lactate, succinate, glycine, and glutamate, dextrose, glycerol, water, as well as combinations thereof. The compositions can also include other components, such as dispersion media, antibacterial and antifungal agents, isotonic and absorption delaying agents, and the like that are physiologically compatible. Isotonic agents include, for example, sugars such as dextrose, polyalcohols such as mannitol, sorbitol, or salts such as sodium chloride in the composition. The composition can also include minor amounts of auxiliary substances such as wetting or emulsifying agents, preservatives or buffers, which enhance the shelf life or effectiveness of the composition.

The components and/or the resulting composition can be sterilized prior to use using various techniques known in the art. Sterile injectable mixtures can be prepared by incorporating the active compound(s) in a therapeutically effective or beneficial amount in an appropriate solvent with one or a combination of ingredients, as required, followed by aseptic filtrations to yield a sterile formulation. Generally, dispersions are prepared by incorporating a compound(s), such as HA, into a sterile vehicle which contains a basic dispersion medium and any required other ingredients. In the case of sterile powders for the preparation of sterile injectable mixtures, some methods can include preparation of vacuum dried and freeze-dried components which yield a powder of the composition plus any additional desired ingredients from a previously sterile-filtered mixture thereof.

Method of Use

In use, the first and second components can be combined intraoperatively, and then delivered to the treatment site, e.g., via injection. In one embodiment, the first and second components can be combined, as discussed above, to form a mixture or composition. Combination of the lyophilized second component, e.g., one or more GAGs, with the first component, e.g., HA, can induce a transient reduction in viscosity of the HA mixture, at least temporarily, allowing greater ease of manipulating and allowing the combined HA/GAG mixture to be placed into a syringe and injected into a patient. In certain embodiments, it may be necessary to wait an amount of time for complete solubilization of the lyophilized component(s) prior to injecting the composition into tissue. The amount of time it takes for the lyophilized second component to solubilized in the first component, or within a solvent, can vary depending on the particular second component used, as well as the molecular weights and concentrations of the components. In general, it can take anywhere from 10 seconds to 30 minutes for the second component to be fully solubilized within the first component, or to be reconstituted with a solvent.

Once the lyophilized component is fully solubilized and the viscosity of the first component, e.g., HA, is significantly reduced, the viscosity will remain reduced for an amount of time, which again can vary depending on the particular materials used, as well as the molecular weight and concentration of the components within the composition. In certain embodiment, once the second component is fully solubilized, the amount of time within which it is desirable to inject the composition into tissue can range from about 1-60 minutes, and more preferably from 1-30 minutes, and more preferably the amount of time can be any one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes or greater or any variable herein.

Delivery Systems

As indicated above, the components used in the present compositions and methods are preferably configured to be combined intraoperatively. The components can thus be provided as part of a kit. In one embodiment, the kit can include a first component, such as HA, and a second component, such as at least one GAG. The kit can also include additional components, as discussed above. The components can be housed in a single container or chamber, or in separate containers or chambers, of a housing, such as a vial or syringe.

In an exemplary embodiment, the components are provided in a single mixing and delivery device. The benefits of a single delivery capability include increasing the speed and ease of drug administration; reducing risk of hospital acquired infection by reducing the number of connections; lowering the risk of drug administration or sequence errors; and quicker delivery of compositions requiring combination prior to administration.

FIG. 1 illustrates one embodiment of a mixing and delivery system that is in the form of a dual chamber syringe 10. As shown, the dual chamber syringe 10 generally include a housing having proximal and distal chambers 12, 14 separated by a valve 16. A plunger 18 is slidably disposed within the proximal chamber 12 and is configured to inject fluid present within the proximal chamber 12 into the distal chamber 14 to thereby mix the components. In one embodiment, the first component, e.g., liquid HA, can be present in the proximal chamber 12 and the second component, e.g., lyophilized GAG, can be present in the distal chamber 14. The plunger 18 can be advanced through the proximal chamber 12 to inject the first component, e.g., liquid HA, into the distal chamber 14 containing the second component, e.g., one or more lyophilized GAGs. In another embodiment, the proximal chamber 12 can contain a solvent, such as water or saline, and the distal chamber 14 can contain all of the components in solid form. For example, the distal chamber 14 can contain lyophilized or solid HA and one or more lyophilized GAGs. The plunger 18 can be advanced through the proximal chamber 12 to inject the solvent into the distal chamber 14, thereby solubilizing the components in the distal chamber 14. Once all components are combined in the distal chamber 14, and any solid is fully solubilized, the mixture can be delivered to tissue, for example by attaching a needle to the distal end of the dual chamber syringe.

Figure 2:
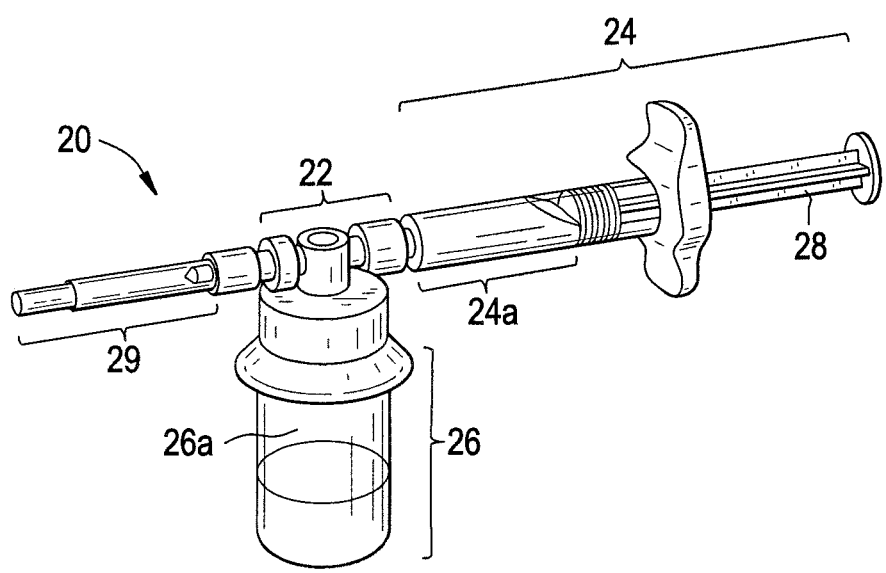
FIG. 2 is a perspective view of another embodiment of a mixing and delivery system for use with the compositions and methods of the present invention.

FIG. 2 illustrates another embodiment of a mixing and delivery system 20, which is sold commercially under the trade name MixJect®. In this embodiment, the system 20 includes a fluid control assembly 22 that is coupled between a syringe 24 and a vial 26. The syringe 24 defines a first chamber 24a which can contain a liquid, such as liquid HA or a solvent, and the vial defines a second chamber 26a which can contain a solid, such as one or more lyophilized GAGs. Deployment of the plunger 28 through the syringe 24 will inject the liquid through the control system and into the vial 26, where the solid will be solubilized by the liquid. Once the components are fully solubilized, the vial 26 can be inverted and the plunger 28 can be retracted to draw the mixture back into the chamber 24a in the syringe 24. The vial 26 can then be removed from the system, and the mixture can be injected from the syringe through a needle 29 and into tissue.

A person skilled in the art will appreciate that any dual chamber systems known in the art can be used, and that the chambers can be side-by-side chambers with separate syringe plungers that mix into a single chamber or linear chambers with a single plunger.

Prefilled syringes can contain the exact deliverable dose of desired compounds and diluents. By way of non-limiting example, the prefilled syringes can contain volumes from about 0.1 ml, 0.2 ml, 0.3 ml, 0.4 ml, 0.5 ml, 0.6 ml, 0.7 ml, 0.8 ml, 0.9 ml, 1.0 ml, 1.5 ml, 2 ml, 2.5 ml, 3 ml, 3.5 ml, 4 ml, 4.5 ml, 5 ml, 5.5 ml, 6 ml, 6.5 ml, 7 ml, 7.5 ml, 8 ml, 8.5 ml, 9 ml, 9.5 ml, 10 ml or more, or any derivative thereof.

Treatment

The HA as well as the GAGs useful in the method and compositions can be administered, for in vivo application, parenterally by injection or by gradual perfusion over time independently or together. Administration may be intravenously, intraperitoneally, intramuscularly, subcutaneously, intra-articular, intracavity, or transdermally. Examples of symptoms or diseases, in which the composition and methods can exert activity in treating articular disorders, include arthritis caused by infections, injuries, allergies, metabolic disorders, etc., rheumatoids such as chronic rheumatoid arthritis, and systemic lupus erythematosus; articular disorders accompanied by gout, arthropathy such as osteoarthritis, internal derangement, hydrarthrosis, stiff neck, lumbago, etc. Varying the effects depending on the use of the composition or the types of diseases to be treated, the agent can exert desired prophylactic and alleviative effects, or even therapeutic effects on swelling, pain, inflammation, and destroying of articulations without seriously affecting living bodies. The composition for treating articular disorder can be used to prevent the onset of articulation disorders, as well as to improve, alleviate, and cure the symptoms after their onsets.

The methods of treatment can include directly injecting the compositions into the target area, such as a joint. Injections can be performed as often as daily, weekly, several times a week, bi-monthly, several times a month, monthly, or as often as needed as to provide relief of symptoms. For intra-articular use, from about 0.1 to about 500 mg per joint, depending on the size of the joint and severity of the condition, can be injected. The frequency of subsequent injections into a given joint are spaced to the time of recurrence of symptoms in the joint. Illustratively, dosage levels in humans of the composition can be: knee, about 0.1 to about 500 mg per joint injection; shoulder, about 0.1 to about 500 mg per joint injection; metacarpal or proximal intraphalangeal, about 0.1 to about 100 mg. per joint injection; and elbow, about 0.1 to about 300 mg per joint injection.

It will be understood, however, that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

In one embodiment, the medical condition is osteoarthritis (OA) and the composition is administered in a joint space, such as, for example, a knee, shoulder, temporo-mandibular and carpo-metacarpal joints, elbow, hip, wrist, ankle, and lumbar zygapophysial (facet) joints in the spine. The viscosupplementation may be accomplished via a single or multiple intraarticular injections administered over a period of weeks into the knee or other afflicted joints. For example, a human subject with knee OA may receive one, two, or three injections of about 2, 3, 4, 5, 6, 7, 8, 9, 10 ml or more per knee. For other joints, the administered volume can be adjusted based on the size on the joint.

In another exemplary embodiment, a kit is provided having first and second components. The first component can comprise 2 ml of Orthovisc®, which contains 30 mg of hyaluronan, 18 mg of sodium chloride, and up to 2.0 mL of water for injection. The HA has a molecular weight in the range of about 1.0 to 2.9 MDa. The second component can comprise 0.1-100 mg/ml of lyophilized bovine derived CS, supplied by, for example, Bioiberica of Barcelona, Spain and lyophilized using the protocol discussed above. The two components can be combined, e.g., using the aforementioned delivery systems, to solubilize the lyophilized CS. Full solubilization can take about X minutes. Once fully solubilized, the mixture will have a significantly reduced viscosity, allowing the mixture to be injected intra-articularly, e.g., into the knee joint. Injection preferably occurs within 5-30 minutes of solubilization. Additional injections can be once a week for a total of three of four injections. Standard intra-articular injection site preparation, aseptic technique and precautions should be used.

EXPERIMENTAL DATA

Example 1—Lyophilization

A mixture containing 50 mg/ml glucosamine HCl and 50 mg/ml chondroitin sulfate was prepared and filtered with a 0.2 µm filter. The mixture was then filled in 3-mL glass vials at 1 mL/vial and lyophilized. The lyophilized cake appeared to be solid and white. Each lyophilized sample was able to be reconstituted with water, Orthovisc, or other HA gels, for injection. These HA gels were at 10-20 mg/ml concentrations and the HA was sourced from Shiseido and Lifecore. Samples were also able to be reconstituted with other buffers such as PBS.

Example 2—Viscosity

Various amounts of different GAGs were lyophilized, as described above, to form a fluffy white cake. The GAGs include bovine derived CS, supplied by Bioiberica of Barcelona, Spain, heparin, supplied by Sigma-Aldrich of Saint Louis, Mo., and dextran sulfate, supplied by Sigma-Aldrich of Saint Louis, Mo. The lyophilized GAGs were each placed in a 5 ml vial having an outer diameter of about 20.8 mm and a height about 40 mm. 40 mg of non-lyophilized GAGs was also placed in a 5 ml vial having the same dimensions. 2 ml of Orthovisc®, manufactured by Anika Therapeutics of Bedford, Mass. was injected into each vial and the HA was allowed to fully dissolve the GAG. A control containing only 2 ml of Orthovisc® was placed in a vial having the same dimensions.

The amount of time it took to fully solubilize the lyophilized GAG was measured for some of the compositions and the results are set forth below. The viscosity of the mixture is measured by determining the "flow rate," which is used herein to refer to the amount of time it took for the contents of each vial to flow from one end of the vial to the other end of the vial when the vial is turned upside-down. The results are set forth in the Table 1 below. The amount of time it took for the flow rate to increase to 1 minute was also measured and is set forth in the Table 1 below. All results set forth in Table 1 are based on the average of three measurements.

such that the mixture was able to transfer from one end of a vial to the opposite end of the vial in seconds. In most cases, with the exception of heparin and dextran, the viscosity remained at a significantly reduced level for at least about 15 minutes.

Example 3—Viscosity 40 mg of non-lyophilized CS powder, obtained from Bioiberica of Barcelona, Spain, was mixed with 500 µL of water. The solution was then combined with 2 ml of Orthovisc®, manufactured by Anika Therapeutics of Bedford, Mass. After about 1-2 minutes of gentle mixing, the components were fully mixed. The flow rate was measured to be 45 seconds.

500 µL of water was combined with 2 ml of Orthovisc®, manufactured by Anika Therapeutics of Bedford, Mass. After about 3 minutes of gentle mixing, the flow rate was measured to be 26 seconds.

The combination of liquid CS with HA showed a reduced flow rate, as compared to the combination of water and HA. Accordingly, the experiment demonstrates the affects of CS on the viscosity of HA.

Example 4—Solubilization 40 mg of non-lyophilized CS powder was obtained from Bioiberica of Barcelona, Spain, was mixed with 2 ml of Orthovisc®, manufactured by Anika Therapeutics of Bedford, Mass. After about 15-20 minutes of gentle mixing, the CS was fully solubilized in the HA. Localized areas of decreased viscosity were observed during solubilization,

TABLE 1

| Composition | Time to fully solubilize Lyophilized GAG with HA | Flow Rate of Composition After Fully Solubilized | Time for Flow Rate to Increase to a Flow Rate of 1 Minute after fully solubilized |
| --- | --- | --- | --- |
| Control: 2 ml HA (Orthovisc ®) | not measured | 20 minutes | not applicable |
| 4 mg lyophilized CS + 2 ml HA (Orthovisc ®) | not measured | 18 seconds | 2 minutes |
| 40 mg lyophilized CS + 2 ml HA (Orthovisc ®) | 5 minutes | 9 seconds | 15 minutes |
| 60 mg lyophilized CS + 2 ml HA (Orthovisc ®) | not measured | 4 seconds | >30 minutes |
| 80 mg lyophilized CS + 2 ml HA (Orthovisc ®) | 15 minutes | 5 seconds | >30 minutes |
| 50 mg lyophilized Heparin + 2 ml HA (Orthovisc ®) | <1 minute | 7 seconds | 5 minutes |
| 50 mg lyophilized Dextran Sulfate + 2 ml HA (Orthovisc ®) | <1 minute | 12 seconds | 5 minutes |
| 40 mg non-lyophilized CS powder + 2 ml HA (Orthovisc ®) | 15-20 minutes | 2 minutes | Not applicable |

As shown in Table 1, HA alone is extremely viscous, with a flow rate of about 20 minutes for 2 ml of HA to transfer from one end of a 5 ml, 40 mm high vial to the opposite end. When combined with GAG powder as received from the vendor or non-lyophilized GAG, there were localized areas of low viscosity. However, during the time it takes to fully solubilize all the powder, the mixture reverts back to high viscosity. Therefore, there is no time to fully mix the sample and get it back into the syringe of a Mixject system. When combined with a lyophilized GAG, on the other hand, the HA is able to dissolve the GAG relatively quickly and the viscosity was significantly reduced, at least temporarily, however prior to full solubilization the HA gel reverted back to its high viscosity state, preventing transfer of the contents into another syringe for injection.

Similarly, 40 mg of lyophilized CS powder, obtained from Bioiberica of Barcelona, Spain, was mixed with 2 ml of Orthovisc®, manufactured by Anika Therapeutics of Bedford, Mass. After about 5 minutes of gentle mixing, the lyophilized CS was fully solubilized in the HA, and the viscosity of the HA was visibly decreased. The reduced viscosity remained for a sufficient period of time, allowing the mixture to be drawn into a syringe for injection.

Terminology

A "therapeutically effective amount" or "effective amount" is that amount of a agent to achieve a pharmacological effect. The term "therapeutically effective amount" includes, for example, a prophylactically effective amount. An "effective amount" is an amount effective to achieve a desired pharmacologic effect or therapeutic improvement without undue adverse side effects. For example, an effective amount refers to an amount that increases operativity, or increases the ability of the patient to bear load on the joint, or decreases pain, or allows patient to get back to normal activity, or stimulate repair in the bone and cartilage of one or more joints, or reduces joint distortion, pain, swelling, inflammation, or stiffness. The effective amount of an agent will be selected by those skilled in the art depending on the particular patient and the disease level. It is understood that "an effective amount" or "a therapeutically effective amount" can vary from subject to subject, due to variation in metabolism of therapeutic agents such as s and/or prokinetic agents, age, weight, general condition of the subject, the condition being treated, the severity of the condition being treated, and the judgment of the prescribing physician.

"Treat" or "treatment" refers to any treatment of a disorder or disease associated with bone or cartilage disorder, such as preventing the disorder or disease from occurring in a subject which may be predisposed to the disorder or disease, but has not yet been diagnosed as having the disorder or disease; inhibiting the disorder or disease, e.g., arresting the development or progression of the disorder or disease, relieving the disorder or disease, causing regression of the disorder or disease, relieving a condition caused by the disease or disorder, or stopping the symptoms of the disease or disorder. Thus, as used herein, the term "treat" is used synonymously with the term "prevent."

By "co-administered" is meant simultaneous administration in the same formulation or in two different formulations that are combined into one formulation for administration. In one embodiment, the HA and the GAG are co-administered via delivery in the same formulation.

The term "subject" as used herein refers to an animal, preferably a mammal and more preferably humans, horses, and dogs who can benefit from the compositions and methods of the present invention. There is no limitation on the type of animal that could benefit from the present methods. A subject regardless of whether a human or non-human animal may be referred to as an individual, subject, animal, host or recipient. The methods of the present invention have applications in human medicine, veterinary medicine as well as in general, domestic or wild animal husbandry.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical kit, comprising:
    a syringe including a first chamber, a second chamber that is separate from the first chamber, and a plunger, wherein the first and second chambers are separated from each other by a valve;
    a first component disposed within the first chamber, the first component comprising hyaluronic acid having a molecular weight of about 1.0 MDa to about 5.0 MDa; and
    a second component disposed within the second chamber, the second component consisting essentially of a lyophilized glycosaminoglycan, wherein the lyophilized glycosaminoglycan comprises unmodified chondroitin sulfate;
    wherein the plunger is configured to move, relative to the valve, to move the first component into the second chamber so as to combine the first and second components and thereby form a mixture having a viscosity suitable for injection through the syringe for a predetermined period of time.

2. The kit of claim 1, further comprising a needle that is configured to be coupled to a distal end of the syringe;
    wherein the needle is configured to inject the mixture into tissue during the predetermined period of time.

3. The kit of claim 1, wherein the lyophilized glycosaminoglycan comprises chondroitin sulfate.

4. The kit of claim 1, further comprising a third component disposed within the second chamber, the third component comprising glucosamine.

5. The kit of claim 1, wherein the predetermined period of time is in a range of about 1 minute to about 60 minutes.

6. The kit of claim 1, wherein the syringe includes a housing with a sidewall that defines the first and second chambers, the movement of the plunger to move the first component into the second chamber comprises movement of the plunger within the first chamber and the valve is seated in the housing with an outer perimeter of the valve abutting an inner surface of the sidewall along an entire circumference of the inner surface.

7. A medical method, comprising:
    mixing hyaluronic acid and a composition consisting essentially of unmodified lyophilized glycosaminoglycan to form a mixture, wherein the hyaluronic acid has a molecular weight of about 1.0 MDa to 5.0 MDa, and wherein the hyaluronic acid is present in the mixture at a concentration between about 7 mg/ml and about 60 mg/ml by weight of the mixture; and
    injecting the mixture into tissue within a predetermined period of time after the mixing, wherein the mixture, during the predetermined period of time, has a viscosity that is less than a viscosity of the hyaluronic acid prior to the mixing;
    wherein, prior to the mixing, the hyaluronic acid is disposed within a first chamber of a syringe;
    wherein the mixing of the hyaluronic acid and the unmodified lyophilized glycosaminoglycan comprises moving the hyaluronic acid from a first chamber of a syringe to a second chamber of the syringe that is separate from the first chamber; and
    wherein, prior to the mixing, the second chamber has the unmodified lyophilized glycosaminoglycan disposed therein.

8. A medical method, comprising:
    actuating at room temperature the plunger of the kit of claim 1, thereby injecting the first component into the second chamber and combining the first and second components.

9. The method of claim 8, wherein the mixture has a second viscosity after the predetermined period of time, the second viscosity being greater than the viscosity.

10. The method of claim 9, wherein the actuating occurs within the predetermined period of time after the formation of the mixture, and the predetermined period of time is in a range of about 1 minute to about 30 minutes.

11. The kit of claim 1, wherein the valve has a disc shape.

12. The method of claim 8, wherein the first component disposed within the first chamber has a viscosity, and during the predetermined period of time the viscosity of the mixture is less than the viscosity of the first component disposed within the first chamber.

13. The method of claim 8, wherein the first and second components are present within the mixture at a ratio of first component to second component in the range of about 1:0.005 to about 1:100.

14. The method of claim 8, wherein the hyaluronic acid is present in the mixture at a concentration between about 7 mg/ml and about 60 mg/ml by weight of the mixture.

15. The method of claim 8, wherein the actuating occurs within the predetermined period of time after the formation of the mixture, and predetermined period of time is in a range of about 1 minute to about 60 minutes.

16. The method of claim 7, wherein the period of time is about 30 minutes.

17. The method of claim 7, wherein the lyophilized glycosaminoglycan comprises chondroitin sulfate.

18. The method of claim 7, wherein the hyaluronic acid and the lyophilized glycosaminoglycan are mixed at room temperature.

19. The method of claim 7, wherein the period of time is in a range of about 1 minute to about 60 minutes.

20. The method of claim 9, wherein the first and second components are present within the mixture at a ratio of first component to second component in the range of about 1:0.005 to about 1:100; and
   the hyaluronic acid is present in the mixture at a concentration between about 7 mg/ml and about 60 mg/ml by weight of the mixture.

21. The method of claim 7, wherein moving the hyaluronic acid from the first chamber of the syringe to the second chamber of the syringe comprises moving, relative to a valve of the syringe that separates the first and second chambers, a plunger of the syringe within the first chamber.

* * * * *